(12) United States Patent
Tian et al.

(10) Patent No.: US 9,389,221 B2
(45) Date of Patent: Jul. 12, 2016

(54) APPARATUS FOR PROCESSING BIOLOGICAL SAMPLES

(71) Applicants: Feng Tian, Vienna, VA (US); Daniel Liang Zou, Richmond Hill (CA); Lingyun Ji, Wuhan (CN)

(72) Inventors: Feng Tian, Vienna, VA (US); Daniel Liang Zou, Richmond Hill (CA); Lingyun Ji, Wuhan (CN)

( * ) Notice: Subject to any disclaimer, the term of this patent is extended or adjusted under 35 U.S.C. 154(b) by 0 days.

(21) Appl. No.: 14/679,024

(22) Filed: Apr. 5, 2015

(65) Prior Publication Data
US 2015/0285790 A1    Oct. 8, 2015

(30) Foreign Application Priority Data
Apr. 4, 2014    (CN) .......................... 2014 1 0137921

(51) Int. Cl.
| | |
|---|---|
| *G01N 33/53* | (2006.01) |
| *B01L 1/00* | (2006.01) |
| *B01L 3/00* | (2006.01) |
| *G01N 1/38* | (2006.01) |
| *G01N 35/00* | (2006.01) |

(52) U.S. Cl.
CPC .............. *G01N 33/5304* (2013.01); *B01L 1/00* (2013.01); *B01L 3/508* (2013.01); *B01L 3/52* (2013.01); *G01N 33/5302* (2013.01); *B01L 2300/02* (2013.01); *B01L 2300/0672* (2013.01); *B01L 2300/0841* (2013.01); *G01N 1/38* (2013.01); *G01N 2035/00524* (2013.01)

(58) Field of Classification Search
CPC ................... G01N 33/5304; B01L 2300/0672; B01L 2300/0841
See application file for complete search history.

(56) References Cited

U.S. PATENT DOCUMENTS

| | | | | |
|---|---|---|---|---|
| 3,444,710 | A | * 5/1969 | Gaugler | ................. D06F 17/04 68/18 R |
| 4,236,541 | A | * 12/1980 | Cipriani | ................ A23N 12/02 134/104.3 |
| 2013/0203072 | A1 | 8/2013 | Tian et al. | |

FOREIGN PATENT DOCUMENTS

| | | |
|---|---|---|
| CN | 202336449 U * | 7/2012 |
| WO | WO2012057801 A1 | 5/2012 |

* cited by examiner

*Primary Examiner* — P. Kathryn Wright
(74) *Attorney, Agent, or Firm* — Feng Tian

(57) ABSTRACT

The present disclosure provides an automated bioprocessing device, which may comprises a processing machine, one or more removable washing cartridges. The removable washing cartridge may comprise a shell, a sample holder, a washing basin, a waste container, a reagent container, a rotation mechanism, and a poking mechanism. The processing machine may comprise a motor, which may provide power to the inserted removable washing cartridge.

9 Claims, 7 Drawing Sheets

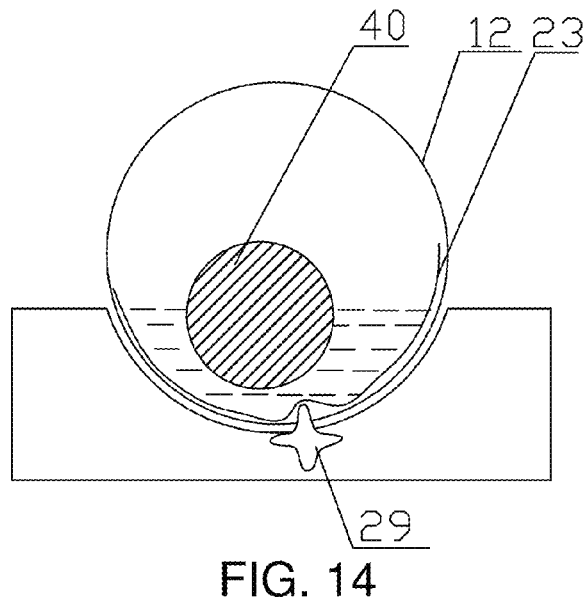
FIG. 14
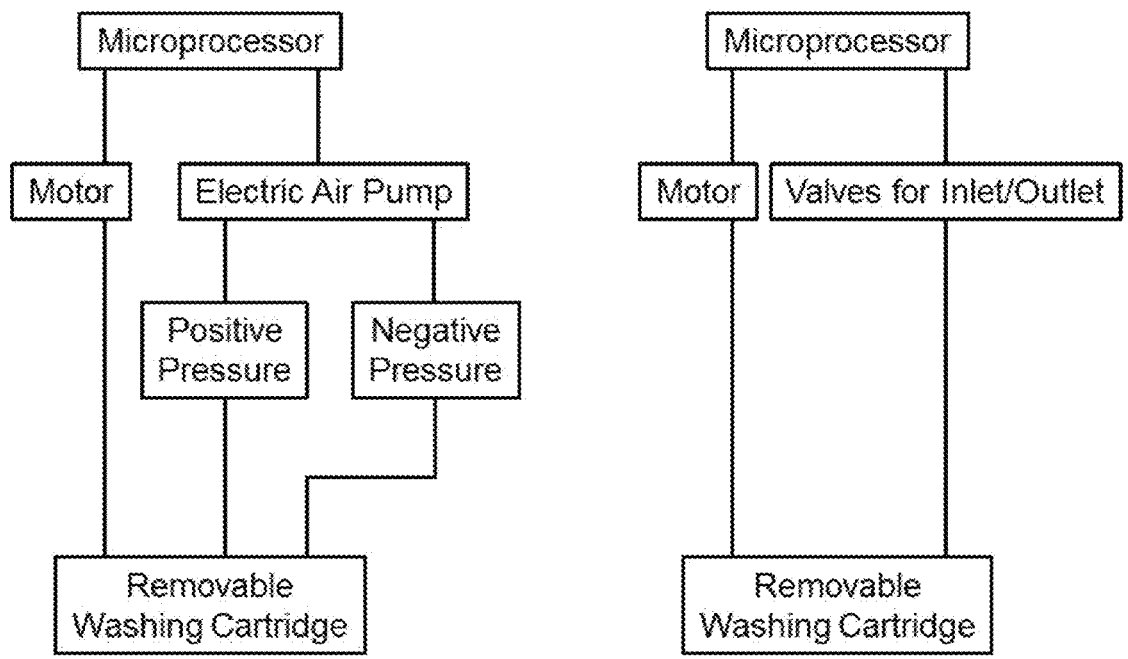
FIG. 15                                   FIG. 16

APPARATUS FOR PROCESSING BIOLOGICAL SAMPLES

CROSS REFERENCE

This present disclosure claims the benefits of Chinese Patent Application No. 201410137921.1 filed on Apr. 4, 2014 which is incorporated herein by reference in its entirety.

FIELD OF THE INVENTION

The present disclosure generally relates to automated device, automated apparatus and automated method for processing biological samples. Specifically, the present disclosure relates to automated apparatus and method for performing blotting assays.

BACKGROUND

Modern biotechnologies require separation, purification and analysis of biological molecules. Consequently, it is routine practice for technicians to treat biological samples with probing molecules, followed by incubation and washing. As a result, traditional incubation and washing of a membrane containing biomolecules of interest in the presence of different solutions are very common in biology labs.

Recently automated devices and apparatuses have been developed to automate such routine washing and incubation steps. Many automated devices and apparatuses rely on either the combination of automated solvent delivery system and horizontal shaker or the combination of automated solvent delivery system and vertical shaker. Even though these machines have achieved automation, one drawback of them has been the requirement of large amount of reagents, including expensive antibody solutions, to fully cover the whole surface of the blot membrane in order to achieve uniformed and effective incubation and washing of the membrane.

Consequently there is a need in the art for new or improved device and apparatus to incubate and wash membranes with less amount of reagent than what is required when using traditional devices, but without reducing the concentration of the antibody solutions. There is also a need for improved methods to accomplish uniformed incubation and washing of membranes without fully covering the surface thereof with reagents/solvents.

SUMMARY OF THE INVENTION

The present disclosure provides an automated bioprocessing device comprising: a) a processing machine; b) one or more removable washing cartridge which comprises: i) a shell; ii) a sample holder within said shell, wherein said sample holder is configured to hold one or more biological samples; iii) a washing basin; iv) a rotation mechanism configured to rotate said sample holder; and v) a poking mechanism configured to agitate said biological sample relative to an interior surface of said sample holder; and c) a control system in said processing machine, wherein said control system is configured to provide power to said removable washing cartridge, wherein said control system comprises one or more motors, and at least one said motor is configured to control said rotation mechanism.

The present disclosure further provides a removable washing cartridge which comprises: a) a shell; b) a sample holder within said shell, wherein said sample holder is configured to hold one or more biological samples; c) a washing basin; d) a rotation mechanism configured to rotate said sample holder; and e) a poking mechanism configured to agitate said biological sample relative to an interior surface of said sample holder.

BRIEF DESCRIPTION OF THE DRAWINGS

FIG. 14 is a schematic view of another exemplary poking mechanism;

FIG. 15 is a high level flow chart of the operation of an exemplary device according to the present disclosure; and FIG. 16 is a high level flow chart of the operation of another exemplary device according to the present disclosure.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and/or combinations.

DETAILED DESCRIPTION

For simplicity and illustrative purposes, the principles of the disclosure are described by referring to an embodiment thereof. The term "about" means plus or minus 10% of the numerical value of the number with which it is being used. Therefore, about 45% means in the range of 35%-55% for example. The articles "a" and "an" are used herein to refer to one or to more than one (i.e., to at least one) of the grammatical object of the article. By way of example, "a container" means one container or more than one container. A "biological sample" refers to any sample to be treated by the automated device/apparatus according to the present disclosure. For example, a membrane containing biological molecules to be analyzed is a biological sample. A western blot membrane is also a biological sample. An air pump refers to an air compressor or a vacuum pump.

In some embodiments, the present disclosure provides systems, devices, apparatuses and methods for automated bioprocessing. Examples of protocols and bioprocessing procedures suitable for the present disclosure include but are not limited to: immunoprecipitation, chromatin immunoprecipitation, recombinant protein isolation, nucleic acid separation and isolation, protein labeling/separation/isolation, cell separation/isolation, and automatic bead based separation.

In a particular embodiment, the disclosure provides automated systems, automated devices, automated cartridges and automated methods of western blot processing. Other embodiments include automated systems, automated devices, automated cartridges and automated methods for separation, preparation and purification of nucleic acids, such as DNA or RNA or fragments thereof, including plasmid DNA, genomic DNA, bacterial DNA, viral DNA and any other DNA or fragments thereof, and for automated systems, automated devices, automated cartridges and automated methods for processing, separation and purification of proteins, peptides and the like.

Figure 1:
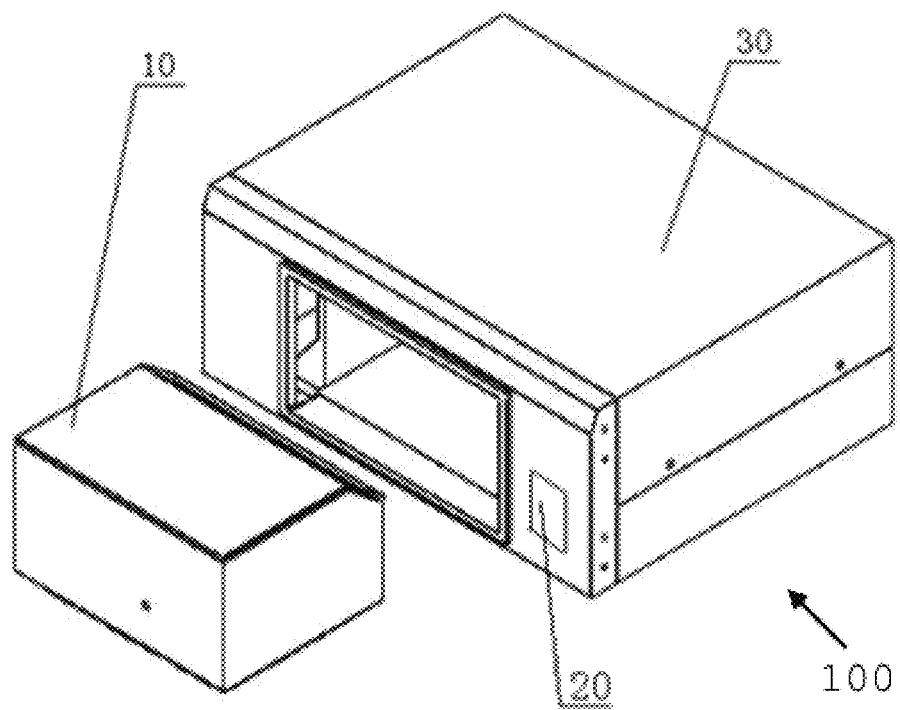
FIG. 1 is an isometric view of an exemplary device according to the present disclosure. The device includes an exemplary removable washing cartridge and an exemplary processing machine.
Figure 2:
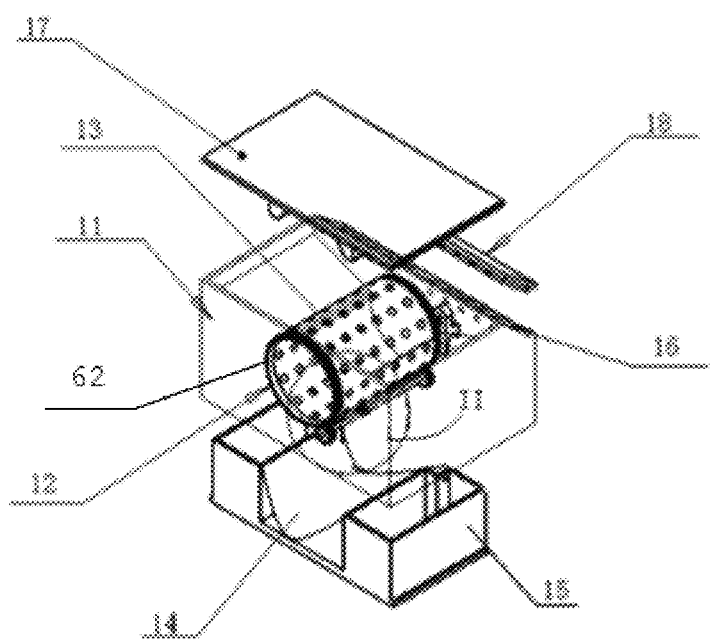
FIG. 2 is a schematic, exploded, perspective view of the exemplary removable washing cartridge 10 in FIG. 1 according to the present disclosure.

Referring now to the drawings, and with specific reference to FIGS. 1 and 2, there is depicted an exemplary automatic device 100 wherein various embodiments of the present disclosure may be utilized. In this example, the device 100 may include a removable washing cartridge 10 and a processing machine 30. The removable washing cartridge 10 may comprise a shell 11, which encloses a sample holder 12, a washing basin 14, a waste container 15, a reagent container 16, a rotation mechanism 50 (not shown), and a poking mechanism 60 (not shown). In addition, the processing machine 30 may include a motor 20 which may provide power to, for example, the rotation mechanism 50, after the removable washing cartridge 10 is inserted into the processing machine 30 and connected with the motor 20.

Figure 4:
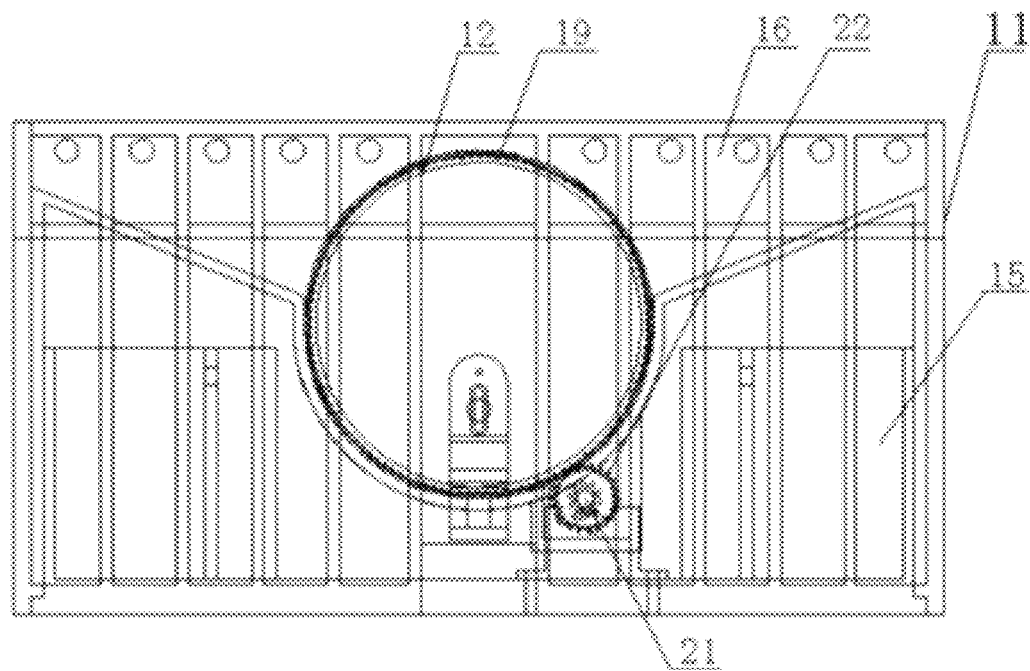
FIG. 4 is a schematic, cross-sectional view of the exemplary removable washing cartridge 10 in FIG. 1 according to the present disclosure.

Further, the sample holder 12 may comprise a cylinder chamber 62, on which there may be a plurality of openings 13 to allow for the free flow of processing fluids into and out of the sample holder 12. During operation, the sample holder 12 may be placed at the washing basin 14, which may adopt a concave configuration to accommodate the sample holder 12. In addition, there may be a reagent container 16 to hold either an incubation solution or a washing solution. A conduit (not shown) may connect the reagent container 16 with the washing basin 14. Meanwhile, a waste container 15 may be located beside or below the sample holder 12. A sample cover 17 is above the sample holder 12, while a reagent cover 18 is above the reagent container 16. FIGS. 2 and 4 demonstrate one embodiment of the relative positions between the shell 11, the sample holder 12, the washing basin 14, the waste container 15, and the reagent container 16.

Figure 3:
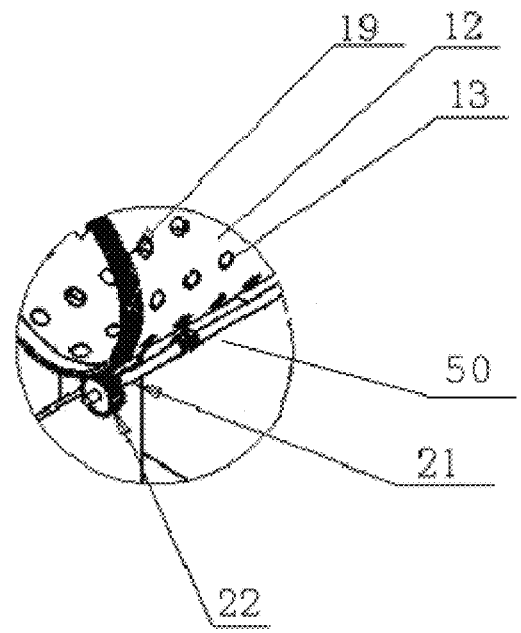
FIG. 3 is an enlarged view of part II in FIG. 2.

There may be multiple ways for the rotation mechanism 50 to actuate either the rims of the sample holder 12 or an end cap on the sample holder 12. Turning now to FIGS. 3-4 for a more detailed disclosure of an embodiment of the rotation mechanism 50 configured to rotate the sample holder 12. The rotation mechanism 50 may comprise a first rotation shaft 21 and a rotation gear 22. In operation, the motor 20 may power the first rotation shaft 21, which in turn actuates the rotation gear 22. When the rotation gear 22 engages a matching gear 19 on the rim of the sample holder 12, the motor may rotate the sample holder 12.

Figure 5:
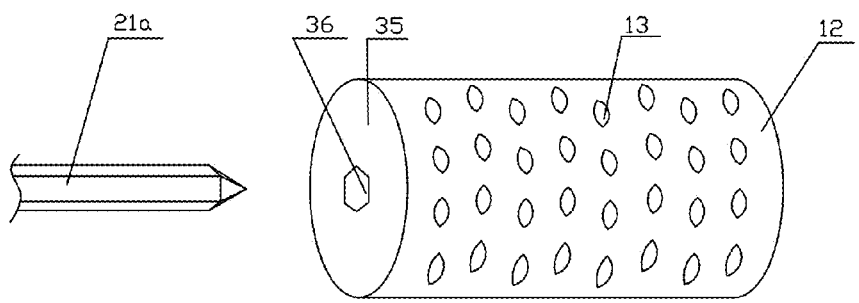
FIG. 5 is a schematic view of an exemplary rotation mechanism.

Referring now to FIG. 5, there is depicted another embodiment, in which the rotation mechanism 50 may actuate the sample holder 12 having a cap 35. More specifically, the rotation mechanism 50 may comprise a second rotation shaft 21a configured to be controlled by the motor 20. In particular, one end of the second rotation shaft 21a may, for example, take the shape of a hexagonal cone, while a first rotation shaft receiver on the center of the cap 35 may take, for example, the shape of a matching hexagon hole to enable the engagement of the second rotation shaft 21 with the sample holder 12, thereby allowing the second rotation shaft 21 to rotate the sample holder 12 when powered by the motor 20.

Figure 6:
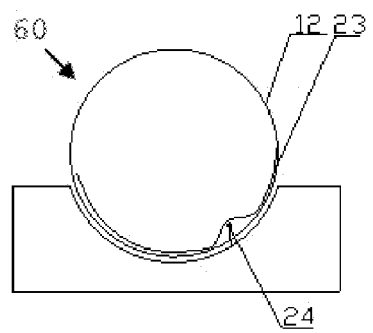
FIG. 6 is a schematic view of an exemplary poking mechanism.

Turning now to FIG. 6, which shows an embodiment of a poking mechanism 60. The poking mechanism 60 may comprise a bendable strip 24, one end of which may be attached to the lower bottom portion of the washing basin 14, the other free end of which may be configured to protrude into and retrieve from openings 13 on the sample holder 12. In operation, when the sample holder 12 is rotated by the rotation mechanism 50, the free end of the bendable strip 24 may interact with the sample holder 12 and adopt a poking form or a non-poking form. On one hand, the bendable strip 24 adopts a poking form when an opening 13 is right above the bendable strip 24 so that the bendable strip 24 may project into the inside of the sample holder 12 and push the biological sample 23 away from the interior surface of the sample holder 12. On the other hand, the bendable strip 24 adopts a non-poking form when no opening 13 is present to allow the protrusion of the bendable strip 24 so that the bendable strip 24 may lie in-between the exterior surface of the sample holder 12 and the surface of the washing basin 14. Due to the alteration of the poking and non-poking forms of the bendable strip 24, the biological sample 23 is agitated constantly when the sample holder is rotating. Consequently, both surfaces of the biological sample 23 may be in full contact with the incubation/washing solution in the washing basin.

Figure 7:
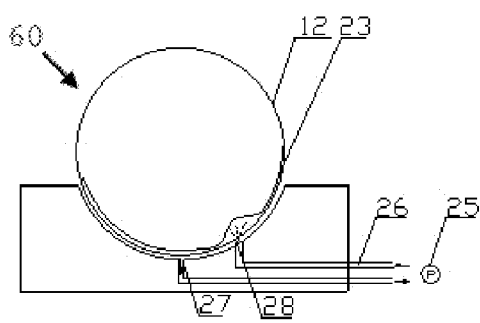
FIG. 7 is a schematic view of another exemplary poking mechanism.

Referring now to FIG. 7, a schematic view of another embodiment of the poking mechanism 60 is shown. The poking mechanism 60 may comprise an automated spray system 70 which may circulate the solution from the washing basin 14 and spray the same solution inside the sample holder 12. The spray system 70 may comprise a first fluid conduit 26, a fluid pump connected to the first fluid conduit 26, a fluid inlet 27, and a fluid outlet 28. Both the fluid inlet 27 and the fluid outlet 28 are at one end of the first fluid conduit 26 and locate below the sample holder 12. In operation, the fluid pump 25 may withdraw fluid from the washing basin 14 via the fluid inlet 27 and the first fluid conduit 26, then spray the withdrawn fluid back into the washing basin 14 through the fluid outlet 28 with sufficient force so that the sprayed fluid may enter the sample holder 12 through openings 13 and push the biological sample 23 away from the interior surface of the sample holder 12, thereby sufficiently wash both surfaces of the biological sample 23.

Figure 8:
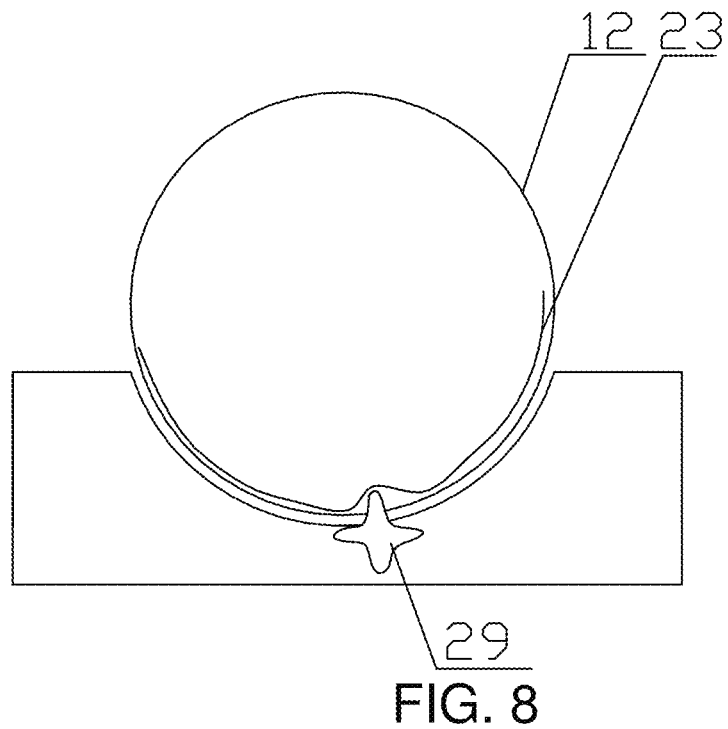
FIG. 8 is a schematic view of still another exemplary poking mechanism.
Figure 9:
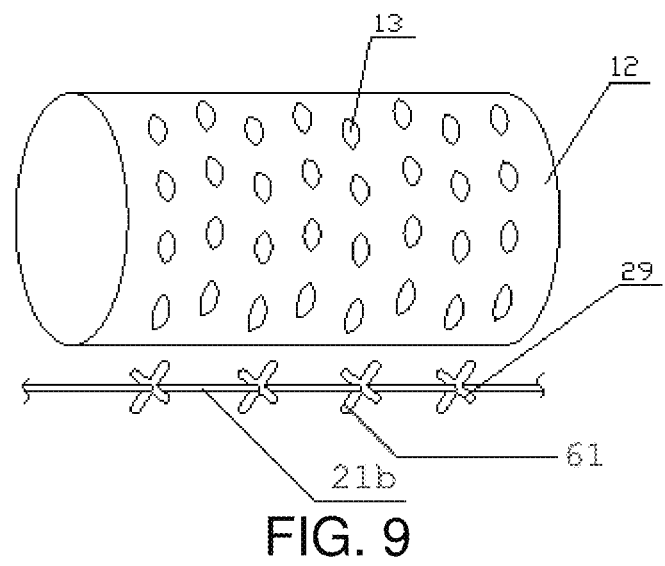
FIG. 9 is a schematic, partial, exploded side view of the same exemplary poking mechanism in FIG. 8.

Turning now to FIGS. 8-9, there is displayed a schematic view of still another embodiment of the poking mechanism 60. The poking mechanism 60 may comprise a plurality of poking gears 29, which are installed on a fourth rotation shaft 21b which is along the direction parallel to the rotational axis of the sample holder 12. It should be noted that the arrangement of the poking gears 29 and openings on the sample holder 12 is configured such that every tooth of gear 29 may protrude through one opening 13 and poke the biological sample 23 away from the interior surface of the sample holder 12, thereby allowing both surfaces of the biological sample 23 in full contact with solutions.

Alternatively, the poking gears 29 may actuate the sample holder 12 so that the poking mechanism may also act as a rotation mechanism. In this dual role, the poking gears 29 is controlled by the fourth rotation shaft 21b which, in turn, is powered by the motor 20. When poking gears 29 engage with the sample holder 12 by protruding through openings 13, the poking gears 29 not only push the biological sample 23 away from the interior surface of the sample holder 12, they also rotate the sample holder 12 within the washing basin 14.

Figure 10:
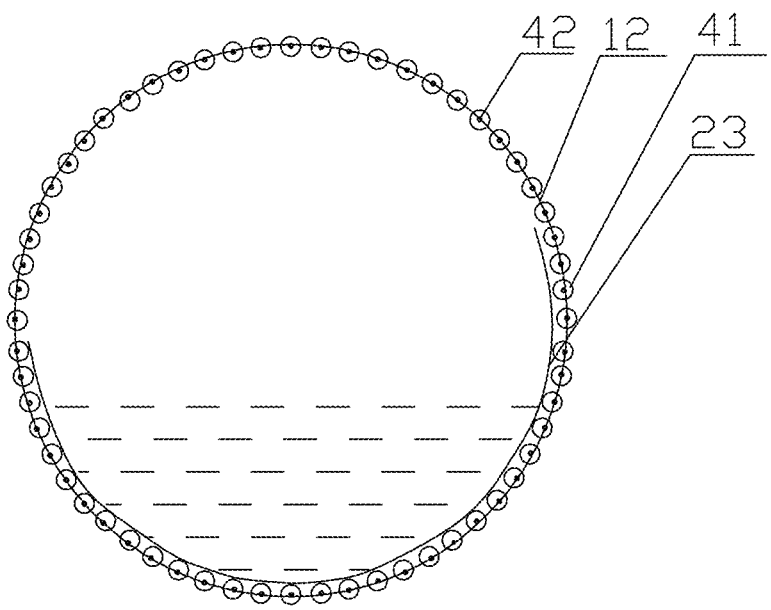
FIG. 10 is a schematic view of another exemplary poking mechanism.

Turning now to FIG. 10, it is shown a schematic view of another exemplary poking mechanism. In this example, the sample holder comprises a frame made of thin rods 42. A corresponding hollow tube 41 encloses each thin rod. Moreover, the hollow tube 41 may rotate around the corresponding thin rod 42 inside the tube 41. The thin rods 42 parallel the rotational axis of the sample holder 12.

In operation, when the sample holder is rotating, hollow tubes 41 may rotate around thin rods 42 as well. At the same time, hollow tubes 41 may have friction against the interior surface of the sample holder 12 so that hollow tubes 41 may poke the biological sample 23 during the hollow tubs' self-rotation. As a result, the biological sample 23 may be constantly rinsed with the solution in the washing basin 14 until both surfaces of the biological sample are effectively washed by the solution.

Figure 11:
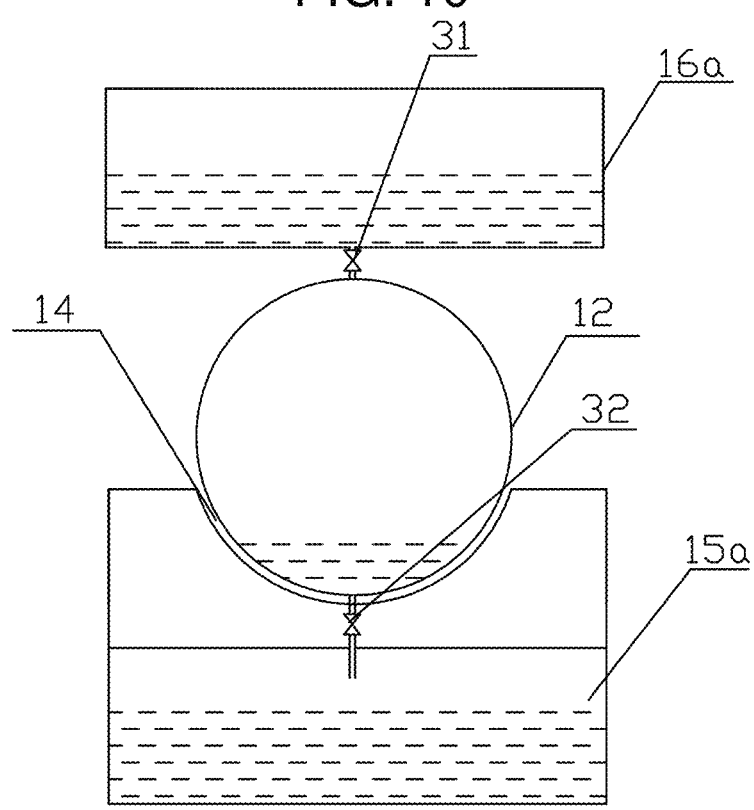
FIG. 11 is a schematic view of an exemplary arrangement of a waste container and a reagent container.

FIG. 11 depicts a schematic view of an exemplary arrangement of a waste container 15a and a reagent container 16a. The processing machine 30 comprises a microprocessor, a motor, and electric valves (including fluid inlet valve 31 and fluid outlet valve 32). In operation, the distribution of fluids (adding and removing) may be accomplished by way of gravity as shown in FIG. 11. For example, a waste container 15a may be installed below the sample holder 12 while a reagent container 16a may be installed above the sample holder 12. In addition, there may be conduits between the waste container 15a and the sample holder 12, and between the reagent container 16a and the sample holder 12, wherein there are valves (including fluid inlet valve 31 and fluid outlet valve 32) connected with the microprocessor along the conduit. In operation, a desired solution is stored in the reagent container 16a. On one hand, when the fluid inlet valve 31 between the reagent container 16a and the sample holder 12 is open, due to gravity, the solution may be added to the washing basin 14. On the other hand, when the fluid outlet valve is open, due to gravity, solution in the washing basin 14 may be discharged into the waste container 15a. As shown in FIG. 16, the microprocessor controls the opening and closing of fluid inlet valve 31 and fluid outlet valve 32.

Figure 12:
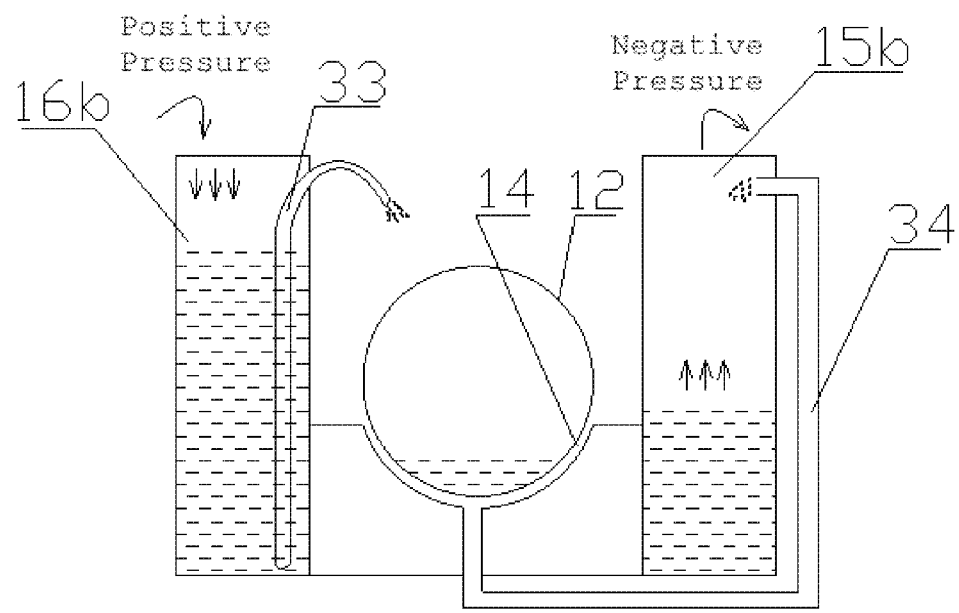
FIG. 12 is a schematic view of another exemplary arrangement of a waste container and a reagent container.

Turning now to FIG. 12, which describes another exemplary arrangement of a waste container 15b and a reagent container 16b. The processing machine 30 comprises a microprocessor, a motor, and electric air pump, wherein the microprocessor controls the motor and the electric air pump so that it provides pressure air or vacuum to the removable washing cartridge 10. For example, after the removable washing cartridge is inserted into the processing machine 30, the shaft of the motor 20 inside the processing machine 30 may mechanically engage the corresponding shaft of the sample holder 12. Consequently, the microprocessor may control the rotation of the motor, thereby rotating the sample holder 12. Meanwhile, air conduits connected with the electric air pump may connect with both the waste container 15b and the reagent container 16b and regulate the air pressure within the containers. Again, the microprocessor controls the electric air pump, thereby creating the corresponding positive pressure or negative pressure in the reagent container 16b and the waste container 15b, respectively.

As depicted in FIG. 12, distribution of solution can be accomplished by providing positive or negative pressure to containers in order to transfer solutions between containers and the washing basin 14. For example, in the presence of positive pressure, pre-stored solution in the reagent container 16b may flow into the washing basin 14 via fluid inlet conduit 33. In addition, due to the negative pressure inside the waste container 15b, the solution in the washing basin 14 may be siphoned into the waste container 15b via the fluid outlet conduit. As shown in FIG. 12, the reagent container 16b comprises a fluid inlet conduit 33. One end of the fluid inlet conduit 33 is at the bottom of the reagent container 16b while the other end of the fluid inlet conduit 33 protrudes outside the reagent container 16b and hangs above the sample holder 12. After the air pressure is increased in the top portion of the reagent container 16b above the solution surface, the solution may be forced to flow into the washing basin 14 via the mouth of the fluid inlet conduit above the sample holder 12.

In one embodiment, when solutions are pre-stored in the reagent container 16b for use, the upper opening of the reagent container 16b may be sealed by films, such as, for example, aluminum foils. Meanwhile the outside tip of the fluid inlet conduit is initially sealed to prevent leakage of the solution pre-stored, but may be broken or opened to allow the flow of solution before the operation of the device.

Turning back to FIG. 12. One end of the fluid outlet conduit 34 may enter the waste container 15b in the upper portion while the other end may connect to the bottom of the washing basin 14 and be configured to receive fluids therefrom. When negative pressure is created inside the waste container 15b, the solution in the washing basin 14 may be siphoned into the waste container 15b via the fluid outlet conduit 34. According to FIG. 15, the positive/negative pressure may be provided by the electric air pump controlled by the microprocessor; the microprocessor and the electric air pump may be installed in the processing machine 30; and the electric air pump may create positive/negative pressure within the reagent container 16b and the waste container 15b.

Figure 13:
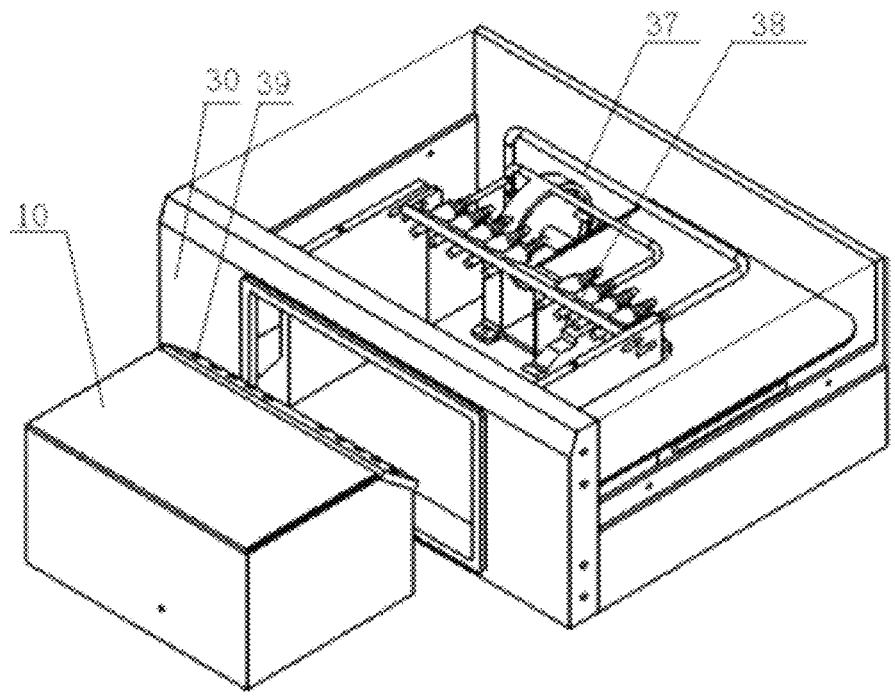
FIG. 13 is a schematic, perspective view of an exemplary connection between an exemplary removable washing cartridge and an exemplary processing machine.

In another embodiment, the removable washing cartridge may be disposable and may engage and communicate with the processing machine 30 after being inserted into the processing machine 30. Referring now to FIG. 13, which displays a schematic, perspective view of an exemplary connection between a removable washing cartridge 10 and a processing machine 30. The connection or engagement between the removable washing cartridge 10 and the processing machine 30 may include the engagement of the motor in the processing machine 30 with the rotation shaft of the sample holder 12; and the secured connection of gas conduits including a gas conduit 37. For example, the gas conduit 37 may connect with a plurality of gas conduit connectors 38. There may be a reagent cover 18 installed on top of the reagent container 16 in the removable washing cartridge with the reagent cover 18 having a 45 degree angle relative to the horizontal plane. There may be a gas opening 39 on the reagent cover 18 corresponding to each individual reagent container 16 so that a user may manually add antibody reagents using appropriate liquid transfer equipment. In addition, these gas openings 39 may facilitate the secured connection between the gas conduit 37 and the reagent container 16 after the disposable removable washing cartridge 10 sliding into and engaging with the processing machine 30.

Turning to FIG. 14, a schematic view of another exemplary poking mechanism 60 is depicted. Compared with another embodiment of poking mechanism in FIG. 6, the poking mechanism in FIG. 14 further comprises a floating object 40 inside the sample holder 12. The presence of the floating object 40 may occupy some volume within the sample holder 12, raise the surface level of the solution inside the sample holder 12, thereby enlarging the incubation area on the biological sample 12 reachable by the same volume of incubation solution when compared with in the absence of the floating object 40. For example, the floating object 40 may comprise a cylinder shape with a diameter about one-half that of the sample holder 12 and with a length smaller than that of the sample holder 12. Alternatively, the floating object 40 may comprise a plurality of ball shape with a diameter about 5 mm. In operation, when the sample holder 12 rotates, the floating object 40 may stay with the solution in the lower portion of the sample holder 12 and swirl around itself. The presence of the floating object 40 may raise the surface level of the solution inside the sample holder 12, hence, cover more surface of the biological sample 23. Not to limit the scope of the present disclosure in any way, it may be postulated that the surface tension may force the solution to cover more surface area of the biological sample 23. Consequently, the biological sample may remain covered with the solution through the operation and be uniformly incubated or washed even in the presence of small incubation solution or washing solution.

Examples

Not to limit the scope of the present disclosure in any way, the followings are examples showing the overall operation of the automatic device according to the present disclosure.

(a) Poking Gear Device Using a Single Cartridge

Configuration:

An exemplary device according to the present disclosure may comprise a processing machine 30 having a microprocessor, a motor, and an electric air pump, and a removable washing cartridge 10 having a plug-in type geared poking mechanism, such as, for example, the poking mechanism 60 comprising poking gear 29 as shown in FIGS. 8-9. The processing machine 30 may comprise two or more pre-installed processing program.

Operating Principle:

After a biological sample 23 is place inside the sample holder 12 and rests on the interior surface of the sample holder 12, the sample holder 12 is placed into the washing basin 14. Then the processing machine 30 powers the sample holder 12 via a motor, keeps it continuously rotating within the washing basin 14, and pumps a solution into and out of the washing basin 14 according to the sequence of a program. It is noted that the volume of solution to be pumped in and pumped out may be determined by the total volume of the pre-stored solution. Because the volume of the air pumped into the containers may be more than the volume of the solution pumped out of the washing basin 14, the excess volume of air may be released from an opening above the washing basin 14. After teeth 61 on the poking gear 29 protrude through openings 13 on the sample holder 12, the poking gear 29, which is below the sample holder 12, may actuate the sample holder 12, keep the sample holder 12 rotating, and keep poking the biological sample 23 to prevent the biological sample 23 from sticking to the interior surface of the sample holder 12. Consequently, solutions may sufficiently cover both surfaces of the biological sample 23 regardless of whether the surface is facing the internal surface of the sample holder 12.

Procedure:

An operator retrieve the removable washing cartridge 10 from the processing machine 30; remove the aluminum foils on top of the reagent containers with pre-stored incubation solutions and washing solutions; and break the sealed outside tip of the fluid inlet conduit. Add required first antibody and second antibody to the corresponding incubation solutions.

Then the operator puts the program selection dial to the desired position. For example, position 1 is a 16-hour incubation/washing program while position 2 is a 4.5-hour fast incubation/washing program.

The operator put the prepared biological sample into the sample holder 12; place the sample holder 12 together with the biological sample into the washing basin 14 of the removable washing cartridge 10; and insert the removable washing cartridge 10 into the processing machine 30.

The processing machine 30 may be turned on after the removable washing cartridge 10 is inserted. According to the position on the program selection dial, the processing machine may keep rotating the sample holder 12, turn on the electric air pump, increase air pressure in containers having desired reagent solutions, and transfer the desired solutions from reagent containers into the washing basin 14.

In the washing basin 14, poking gear may poke the biological sample 23 so that the solution may sufficiently cover both surfaces of the biological sample. After the air conduit secures connection with the waste container, the processing machine activate an air pump to produce negative pressure inside the waste container so that the solution in the washing basin 14 may be siphoned into the waste container via the outlet at the bottom of the washing basin 14.

Later the processing machine create positive pressure in the reagent container having the first antibody and push the first antibody solution into the washing basin 14. After the first antibody reacts sufficiently with the biological sample, the remaining first antibody solution is drained, followed by three washing steps, wherein washing solutions stored in three containers are sequentially pumped into and drained from the washing basin 14.

Then the processing machine pumped the second antibody into the washing basin according to the program. After the second antibody reacts sufficiently with the biological sample, the remaining second antibody solution is drained, followed again by three washing steps. However this time, the last washing solution is not drained but is kept in the washing basin to keep the processed biological sample wet until the operator retrieves the removable washing cartridge 10 by pressing a button.

After the removable washing cartridge 10 is removed from the processing machine, the processing machine may automatically stop. The operator may retrieve the sample holder and the processing biological sample therein. As to the used removable washing cartridge, if it would be used in another operation with the same first and second antibodies, it may be reused after recharging with required reagents/solutions. The obtained biological sample may be subjected to colorimetric or chemiluminescent detections immediately.

(b) Bendable Strip Gravity Device Using a Single Cartridge

Configuration:

An exemplary device according to the present disclosure may comprise a processing machine 30 having a microprocessor, a motor, and an electric valve, and a removable washing cartridge 10 having a bendable strip poking mechanism, such as, for example, the poking mechanism 60 comprising a bendable strip 24 as shown in FIG. 6. The processing machine 30 may comprise two or more pre-installed processing program.

Operating Principle:

After a biological sample 23 is place inside the sample holder 12 and rests on the interior surface of the sample holder 12, the sample holder 12 is placed into the washing basin 14. Then the processing machine 30 powers the sample holder 12 via a motor, keeps it continuously rotating within the washing basin 14, and operates the appropriate valves (for example, fluid inlet valve 31 and fluid outlet valve 32) according the program to introduce solutions into or drain solutions from the washing basin 14. The volume of the solution introduced or drained is determined by the pre-stored volume of each solution. Under the sample holder 12 is placed a bendable strip 24, which, due to its elasticity, may projected into the inside of the sample holder 12 and constantly push the biological sample 23 away from the interior surface of the sample holder 12. As a result, solutions may sufficiently cover both surfaces of the biological sample 23 regardless of whether the surface is facing the interior surface of the sample holder 12.

Procedure:

An operator retrieve the removable washing cartridge 10 from the processing machine 30; remove the aluminum foils on top of the reagent containers with pre-stored incubation solutions and washing solutions; and add required first antibody and second antibody to the corresponding incubation solutions.

Then the operator puts the program selection dial to the desired position. For example, position 1 is a 16-hour incubation/washing program while position 2 is a 4.5-hour fast incubation/washing program.

The operator put the prepared biological sample into the sample holder 12; place the sample holder 12 together with the biological sample into the washing basin 14 of the removable washing cartridge 10; and insert the removable washing cartridge 10 into the processing machine 30.

The processing machine 30 may be turned on after the removable washing cartridge 10 is inserted. According to the position on the program selection dial, the processing machine may keep rotating the sample holder 12, operate the appropriate valves, and transfer the desired solutions from reagent containers into the washing basin 14.

In the washing basin 14, the bendable strip 24 may poke the biological sample 23 so that the solution may sufficiently cover both surfaces of the biological sample. In addition, the processing machine may operate the fluid outlet valve so that solutions in the washing basin 14 may be drained into the waste container via the fluid outlet at the bottom of the washing basin 14.

Later, the processing machine operates the fluid inlet valve for the container storing the first antibody solution and allows the first antibody solution to flow into the washing basin 14. After the first antibody reacts sufficiently with the biological sample, the remaining first antibody solution is drained, followed by three washing steps, wherein washing solutions stored in three containers are sequentially pumped into and drained from the washing basin 14.

Then the processing machine operates the fluid inlet valve for the container storing the second antibody solution and allows the second antibody solution to flow into the washing basin 14 according to the program. After the second antibody reacts sufficiently with the biological sample, the remaining second antibody solution is drained, followed again by three washing steps. However this time, the last washing solution is not drained but is kept in the washing basin with constant rotation of the sample holder to keep the processed biological sample wet until the operator retrieves the removable washing cartridge 10 by pressing a button.

After the removable washing cartridge 10 is removed from the processing machine, the processing machine may automatically stop. The operator may retrieve the sample holder and the processing biological sample therein. As to the used removable washing cartridge, if it would be used in another operation with the same first and second antibodies, it may be reused after recharging with required reagents/solutions. The obtained biological sample may be subjected to colorimetric or chemiluminescent detections immediately.

(c) Poking Gear Device Using Multiple Cartridges

Configuration:

An exemplary device according to the present disclosure may comprise a processing machine 30 having a microprocessor, a motor, and an electric air pump, and a removable washing cartridge 10 having a plug-in type geared poking mechanism, such as, for example, the poking mechanism 60 comprising poking gear 29 as shown in FIGS. 8-9. The processing machine 30 may comprise two or more pre-installed processing program.

A motor in the processing machine may use mechanical engagement to operate and rotate multiple sample holders, for example, 4 sample holders.

A set of air compressor/vacuum pump system may operate multiple removable washing cartridges to regulate the transfer of solutions by varying the air pressure accordingly. For example, four removable washing cartridge may be used at the same time.

Operating Principle:

After each biological sample 23 is place inside the corresponding sample holder 12 and rests on the interior surface of the same sample holder 12, sample holders are placed into the corresponding washing basins 14. Then the processing machine 30 powers sample holders 12 via a motor, keeps them continuously rotating within washing basins 14, and pumps solutions into and out of washing basins 14 according to the sequence of a program. It is noted that the volume of solution to be pumped in and pumped out may be determined by the total volume of the pre-stored solution. Because the volume of the air pumped into the containers may be more than the volume of the solution pumped out of washing basins 14, the excess volume of air may be released from openings above washing basins 14.

After teeth 61 on poking gears 29 protrude through openings 13 on each sample holder 12, each poking gear 29, which is below each corresponding sample holder 12, may actuate each sample holder 12, keep each sample holder 12 rotating, and keep poking each biological sample 23 to prevent each biological sample 23 from sticking to the interior surface of each sample holder 12. Consequently, solutions may sufficiently cover both surfaces of each biological sample 23 regardless of whether the surface is facing the interior surface of each sample holder 12.

Procedure:

An operator retrieve the removable washing cartridge 10 from the processing machine 30; remove the aluminum foils on top of the reagent containers with pre-stored incubation solutions and washing solutions; and break the sealed outside tip of the fluid inlet conduit. Add required first antibody and second antibody to the corresponding incubation solutions.

Then the operator puts the program selection dial to the desired position. For example, position 1 is a 16-hour incubation/washing program while position 2 is a 4.5-hour fast incubation/washing program.

The operator may use only one removable washing cartridge 10 or multiple removable washing cartridges 10 simultaneously in the same operation.

The operator put the prepared biological sample into the sample holder 12; place the sample holder 12 together with the biological sample into the washing basin 14 of the removable washing cartridge 10; and insert the removable washing cartridge 10 into the processing machine 30.

The processing machine 30 may be turned on after the removable washing cartridge 10 is inserted. Depending on program selected by the operator on the processing machine, the processing machine may keep rotating the sample holder 12, turn on the electric air pump, increase air pressure in containers having desired reagent solutions, and transfer the desired solutions from reagent containers into the washing basin 14.

In the washing basin 14, poking gear may poke the biological sample 23 so that the solution may sufficiently cover both surfaces of the biological sample. After the air conduit secures connection with the waste container, the processing machine activate an air pump to produce negative pressure inside the waste container so that the solution in the washing basin 14 may be siphoned into the waste container via the outlet at the bottom of the washing basin 14.

Later the processing machine create positive pressure in the reagent container having the first antibody and push the first antibody solution into the washing basin 14. After the first antibody reacts sufficiently with the biological sample, the remaining first antibody solution is drained, followed by three washing steps, wherein washing solutions stored in three containers are sequentially pumped into and drained from the washing basin 14.

Then the processing machine pumped the second antibody into the washing basin according to the program. After the second antibody reacts sufficiently with the biological sample, the remaining second antibody solution is drained, followed again by three washing steps. However this time, the last washing solution is not drained but is kept in the washing basin to keep the processed biological sample wet until the operator retrieves the removable washing cartridge 10 by pressing a button.

After the removable washing cartridge 10 is removed from the processing machine, the processing machine may automatically stop. The operator may retrieve the sample holder and the processing biological sample therein. As to the used removable washing cartridge, if it would be used in another operation with the same first and second antibodies, it may be reused after recharging with required reagents/solutions. The obtained biological sample may be subjected to colorimetric or chemiluminescent detections immediately.

While the invention has been described with reference to certain embodiments, it will be understood by those skilled in the art that various changes may be made and equivalents may be substituted for elements thereof without departing from the scope of the invention. In addition, many modifications may be made to adapt to a particular situation or material to the teachings of the present disclosure without departing from the essential scope thereof. Therefore, it is intended that the invention not be limited to the particular embodiments disclosed as the best mode contemplated for carrying out this invention, but that the invention will include all embodiments falling within the scope of the appended claims.

We claim:

1. An automated bioprocessing device comprising:
   a) a processing machine including a microprocessor and an electric pump configured to be controlled by the microprocessor to provide either positive or negative pressure to either a reagent container or a waste container;
   b) one or more removable washing cartridge, wherein said removable washing cartridge comprises:
      i) a shell;
      ii) a sample holder within said shell, wherein said sample holder is configured to hold one or more biological samples, the sample holder includes a cylinder chamber and a plurality of openings on the cylinder chamber;
      iii) a washing basin disposed within the shell and configured to at least partially surround the sample holder;
      iv) a rotation mechanism disposed within the shell and configured to rotate said sample holder; and
      v) a poking mechanism disposed within the shell and includes a plurality of poking gears arranged along a rotation shaft and located at the bottom of the washing basin, each gear having teeth arranged such that a tooth on the poking gear is configured to pass through the opening of the cylinder chamber and agitate the biological sample; and
   c) a control system in said processing machine, wherein said control system is configured to provide power to said removable washing cartridge, said control system comprises one or more motors, and at least one said motor is configured to control said rotation mechanism.

2. The device of claim 1, wherein said removable washing cartridge further comprises:
   a) one or more waste containers;
   b) one or more reagent containers; and
   c) one or more first fluid conduits configured to connect with said washing basin.

3. The device of claim 1, wherein said rotation mechanism further comprises:
   a) a first rotation shaft;
   b) a rotation gear configured to be actuated by said first rotation shaft; and
   c) a matching gear on said sample holder, wherein said matching gear matches with said rotation gear, and said matching gear is configured to be actuated by said rotation gear.

4. The device of claim 1, wherein said rotation mechanism further comprises:
   a) a second rotation shaft;
   b) a cap on an end of said sample holder; and
   c) a first rotation shaft receiver on said cap, wherein said first rotation shaft receiver is configured to engage with said second rotation shaft and to rotate said sample holder.

5. The device of claim 2, wherein
   a) said reagent container is above said sample holder;
   b) said waste container is below said sample holder; and
   c) said conduit further comprises a fluid inlet valve and a fluid outlet valve.

6. A removable washing cartridge comprises:
   a) a shell;
   b) a sample holder within said shell, wherein said sample holder is configured to hold one or more biological samples, the sample holder includes a cylinder chamber and a plurality of openings on the cylinder chamber;
   c) a washing basin disposed within the shell and configured to at least partially surround the sample holder;
   d) a rotation mechanism disposed within the shell and configured to rotate said sample holder; and
   e) a poking mechanism disposed within the shell and includes a plurality of poking gears arranged along a rotation shaft and located at the bottom of the washing basin, each gear having teeth arranged such that a tooth on the poking gear is configured to pass through the opening of the cylinder chamber and agitate the biological sample.

7. The removable washing cartridge of claim 6 further comprises:
   a) one or more waste containers;
   b) one or more reagent containers; and
   c) one or more first fluid conduits configured to connect with said washing basin.

8. The removable washing cartridge of claim 6, wherein said rotation mechanism further comprises:

a) a first rotation shaft;
b) a rotation gear configured to be actuated by said first rotation shaft; and
c) a matching gear on said sample holder, wherein said matching gear matches with said rotation gear, and said matching gear is configured to be actuated by said rotation gear.

9. The removable washing cartridge of claim 6, wherein said rotation mechanism further comprises:
a) a second rotation shaft;
b) a cap on an end of said sample holder; and
c) a first rotation shaft receiver on said cap, wherein said second rotation shaft is configured to engage said first rotation shaft receiver and rotate said sample holder.

* * * * *